United States Patent
Marie et al.

(10) Patent No.: US 8,709,129 B2
(45) Date of Patent: Apr. 29, 2014

(54) COMPOUNDS USEFUL AS LIGANDS OF ACTINIDES, THEIR SYNTHESIS AND THEIR USES

(75) Inventors: Cécile Marie, Avignon (FR); Manuel Miguirditchian, Avignon (FR); Julia Bisson, Nantes (FR); Denis Guillaneux, Villeneuve les Avignon (FR); Didier Dubreuil, Port Saint Pere (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/386,340

(22) PCT Filed: Jul. 16, 2010

(86) PCT No.: PCT/EP2010/060280
§ 371 (c)(1),
(2), (4) Date: Apr. 17, 2012

(87) PCT Pub. No.: WO2011/009814
PCT Pub. Date: Jan. 27, 2011

(65) Prior Publication Data
US 2012/0186396 A1  Jul. 26, 2012

(30) Foreign Application Priority Data

Jul. 21, 2009  (FR) .................................... 09 55069

(51) Int. Cl.
*C22B 60/00* (2006.01)
*C07D 401/14* (2006.01)

(52) U.S. Cl.
USPC .............................................. 75/393; 546/257

(58) Field of Classification Search
CPC ............................. C22B 60/00; C07D 401/14
See application file for complete search history.

(56) References Cited

U.S. PATENT DOCUMENTS

| 2009/0184051 A1 | 7/2009 | Heres et al. |
| 2011/0002823 A1 | 1/2011 | Miguirditchian et al. |

FOREIGN PATENT DOCUMENTS

| EP | 0850322 B1 | 5/2001 |
| WO | 2007118904 A1 | 10/2007 |
| WO | 2008049807 A1 | 5/2008 |

OTHER PUBLICATIONS

Galaup, et al., "Direct Access to Terpyridine-Containing Polyazamacrocycles as Photosensitizing Ligands for Eu (III) Luminescence in Aqueous Media", Journal of Organic Chemistry, 2005, 70(6), 2274-2284.

Thummel, et al., "N-Oxides of 2, 2':6', 2"—Terpyridine", Journal of Organic Chemistry 1985, 50(19), 3635-3636.

Fife, "Regoselective Cyanation of Pyridine 1—Oxides with Trimethysilanecarbonitrile: A Modified Reissert-Henze Reation", Journal of Organic Chemistry 1983, 48(8), 1375-1377.

Newkome, et al., "Metallomicellanois: Incorporation of Ruthenium (II)-2,2':6',2"-Terpyridine Triads into Cascade Polymers", Journal of the Chemical Society, Chemical Communications 1993, 925-927.

Case, et al., "The Preparation of Some Substituted 2, 6-Bis-(2-pyridyl)-pyridines", Journal of the American Chemical Society 1956, 78, 5842-5844.

Constable, et al., "Synthesis and Co-ordination Behaviour of 6', 6"-Bis (2-pyridyl) -2,2':4,4":2",2"'-quaterpyridine; 'Back-to-back' 2,2':6',2"-Terpyridine", Journal of the Chemical Society, Dalton Transactions 1990, 1405-1409.

Preliminary Search Report issued on Mar. 5, 2010 for French Application No. FR 0955069.

Petitjean, et al., "Dynamic Devices, Shape Switching and Substrate Binding in Ion-controlled nanomechanical molecular tweezers", Journal of the American Chemical Society, American Chemical Society, New York, USA, vol. 126, No. 21, Jun. 2, 2004, pp. 6637-6647.

International Search Report issued on Oct. 6, 2010 for International Application No. PCT/EP2010/060280.

*Primary Examiner* — Yun Qian
(74) *Attorney, Agent, or Firm* — Knobbe, Martens, Olson & Bear, LLP (57) ABSTRACT

The invention relates to novel compounds which are useful as ligands of actinides, to the synthesis of these compounds and to their uses.

These compounds fit the general formula (I) hereafter:

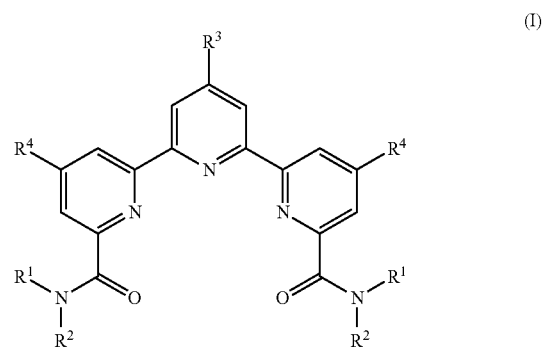

wherein $R^1$ and $R^2$, either identical or different, represent H, a linear or branched, saturated or unsaturated $C_1$-$C_{12}$ hydrocarbon group, a phenyl, benzyl, diphenyl or tolyl group; $R^3$ represents H, a linear or branched, saturated or unsaturated $C_1$-$C_{12}$ hydrocarbon group, a phenyl, tolyl or linear or branched $C_1$-$C_{12}$ alkoxy group; while $R^4$ represents H, a linear or branched, saturated or unsaturated $C_1$-$C_{12}$ hydrocarbon group, a phenyl or tolyl group.

Field of applications: the processing of used nuclear fuels via a hydrometallurgical route.

6 Claims, 3 Drawing Sheets

COMPOUNDS USEFUL AS LIGANDS OF ACTINIDES, THEIR SYNTHESIS AND THEIR USES

RELATED APPLICATIONS

This application is a U.S. National Phase of International Application No. PCT/EP2010/060280, filed Jul. 16, 2010, designating the U.S., and published in French as WO 2011/009814 on Jan. 27, 2011 which claims the benefit of French Patent Application No. 0955069 filed Jul. 21, 2009.

TECHNICAL FIELD

The present invention relates to novel compounds which are useful as ligands of actinides.

It also relates to the synthesis of these compounds and to their uses.

The compounds according to the invention, which have a more pronounced affinity for actinides than for lanthanides and which are capable of extracting actinides from a strongly acid aqueous solution such as a nitric acid solution with a molarity at least equal to 2, may notably be used in the field of the processing of used nuclear fuels via a hydrometallurgical route, in particular for separating in a grouped way, the whole of the actinides (uranium, plutonium, neptunium, americium and/or curium), from the lanthanides present in dissolution solutions of used nuclear fuels.

BACKGROUND

In order to separate in a grouped way the plutonium, neptunium, americium, curium and possibly the uranium from the lanthanides present in a dissolution solution of a used nuclear fuel, two methods have been recently proposed which use as an extractant, a malonamide such as N,N'-dimethyl-N,N'-dioctylhexyl-ethoxymalonamide (or DMDOHEMA) or a diglycolamide such as N,N,N',N'-tetraoctyl-3-oxapentanediamide (or TODGA).

These methods are respectively described in the international PCT applications published under the Nos. WO 2007/118904 (reference [1]) and WO 2008/049807 (reference [2]).

It turns out that the extractants having donor oxygen atoms such as malonamides and diglycolamides do not allow extraction from an acid aqueous solution containing both actinides and lanthanides, of the actinides without extracting at the same time the lanthanides.

Consequently, the methods described in the aforementioned references first of all comprise a step aiming at co-extracting the actinides and lanthanides from the aqueous solution in which they are found, by means of an organic phase which contains the malonamide or the diglycolamide. This co-extraction step is followed by a step aiming at selectively stripping the actinides from the organic phase, which is achieved by means of a slightly acid aqueous phase, i.e. with a pH comprised between 2 and 3, and containing a complexing agent, for example a polyaminocarboxylic acid. The lanthanides are then retained in the organic phase either by the presence in this organic phase of an acid extractant of the phosphoric acid type (reference [1]) or by the presence in the slightly acid aqueous phase of nitrate ions (reference [2]). A step then follows aiming at stripping the lanthanides from the organic phase in order to recover these lanthanides in an aqueous phase capable of being subsequently subject to vitrification operations on the one hand and, at stripping the organic phase of radio-elements with view to its re-use on the other hand.

Now, in the perspective of developing novel methods for processing used nuclear fuels, it would be desirable to have extractants allowing grouped isolation of all the actinides present in dissolution solutions of used nuclear fuels. The methods for processing used nuclear fuels would notably be simplified and therefore less costly to apply.

Compounds are known which have a larger affinity for actinides and in particular for actinides(III), than for lanthanides.

These are nitrogen-containing polyaromatic compounds such as 2,2':6',2"-terpyridine and certain of its alkylated derivatives, 2,4,6-tri(2-pyridinyl)-1,3,5-triazine (or TPTZ), 2,6-bis(pyridin-2-yl)-4-amino-1,3,5-triazine (or ADPTZ) and 2,6-bis(1,2,4-triazinyl)pyridines, picolinamides, dipicolinamides and bipyridines with amide substitutions.

However, none of these compounds seems to be able to be used in an industrial process which would aim at grouped separation of the whole of the actinides present in dissolution solutions of used nuclear fuels from the lanthanides also present in these solutions, either because they are quite simply incapable of extracting alone the actinides from a strongly acid aqueous phase (which, for example, is the case of 2,2':6',2"-terpyridine and of its alkylated derivatives, of TPTZ, of ADPTZ and of picolinamides which are only capable of extracting them at a low acidity and in a synergistic mixture with another extractant, typically α-bromodecanoic acid), or because they have a too low loading capacity (this is, for example, the case of 2,6-bis(1,2,4-triazinyl)pyridines), or further because they require being in solution in a polar, halogenated and toxic diluent such as chloroform or meta-nitrotrifluorotoluene, and therefore may be hardly used in an industrial process (this is, for example, the case of dipicolinamides).

The Inventors therefore set themselves the goal of providing novel compounds which not only have larger affinity for actinides than for lanthanides but are further capable of extracting from a strongly aqueous acid solution the whole of the actinides present in this solution so that these compounds allow grouped isolation of all the actinides present in different degrees of oxidation in a dissolution solution of used nuclear fuels.

Further they set themselves the goal that the relevant compounds may be used in solution in a diluent capable of being used in an industrial process for processing used nuclear fuels.

DESCRIPTION OF CERTAIN INVENTIVE ASPECTS

These goals and further other ones are achieved by the invention which firstly proposes a compound which fits the general formula (I) hereafter:

(I)

wherein:
R$^1$ and R$^2$, either identical or different, represent a hydrogen atom, a linear or branched, saturated or unsaturated $C_1$-$C_{12}$ hydrocarbon group, a phenyl group, a benzyl group, a biphenyl group or a tolyl group;

$R^3$ represents a hydrogen atom, a linear or branched, saturated or unsaturated $C_1$-$C_{12}$ hydrocarbon group, a phenyl group, a tolyl group or a linear or branched $C_1$-$C_{12}$ alkoxy group; while $R^4$ represents a hydrogen atom, a linear or branched, saturated or unsaturated $C_1$-$C_{12}$ hydrocarbon group, a phenyl group or a tolyl group.

Thus, the compound according to the invention has the feature of comprising both a terpyridine unit and two amide groups, the latter being respectively located on one of the side pyridine rings of the terpyridine unit.

In the foregoing and in the following, by "linear or branched, saturated or unsaturated, $C_1$-$C_{12}$ hydrocarbon group", is meant any alkyl group with a linear or branched chain, which comprises at least 1 carbon atom but not more than 12 carbon atoms and any alkenyl or alkynyl group, with a linear or branched chain, which comprises at least 2 carbon atoms and not more than 12 carbon atoms.

Such hydrocarbon groups are, for example, methyl, ethyl, n-propyl, isopropyl, butyl such as n-butyl, sec-butyl or isobutyl, pentyl such as n-pentyl, or sec-pentyl or isopentyl, hexyl such as n-hexyl or isohexyl, octyl such as n-octyl or isooctyl, decyl such as n-decyl or isodecyl, dodecyl, ethylenyl, propylenyl, butenyl, pentenyl, hexenyl, methyl-pentenyl, buta-1,3-dienyl, octenyl, decenyl, dodecenyl, ethynyl, propynyl, butynyl, pentynyl, hexynyl, octynyl, decynyl, dodecynyl groups, etc.

Moreover, by a "linear or branched $C_1$-$C_{12}$ alkoxy group" is meant any O-alkyl group in which the alkyl group is with a linear or branched chain and comprises from 1 to 12 carbon atoms.

Such an alkoxy group is, for example, a methoxy, ethoxy, n-propoxy, isopropoxy, butoxy such as n-butoxy, sec-butoxy or isobutoxy, pentoxy such as n-pentoxy, sec-pentoxy or isopentoxy, hexyloxy such as n-hexyloxy or isohexyloxy, octoxy such as n-octoxy or iso-octoxy, decyloxy such as n-decyloxy or isodecyloxy, dodecyloxy group etc.

According to the invention the compound preferably fits the general formula (I) wherein:

$R^1$ and $R^2$, either identical or different represent a hydrogen atom, a linear or branched $C_1$-$C_{12}$ alkyl chain or a phenyl group;

$R^3$ represents a hydrogen atom or a linear or branched $C_1$-$C_{12}$ alkyl or alkoxy group; while $R^4$ represents a hydrogen atom or a linear or branched $C_1$-$C_{12}$ alkyl group.

Furthermore, it is preferred that, in the general formula (I), $R^3$ and $R^4$ represent a hydrogen atom for the simple reason that the synthesis of terpyridines including no other substituent than both amide groups borne by the side pyridine rings of the terpyridine unit, is simpler to apply than that of terpyridines with more substitutions.

Also, it is preferred that, in the general formula (I), $R^1$ and $R^2$ be identical, in which case they advantageously represent a linear or branched $C_1$-$C_{12}$ alkyl chain and even better a chain with an even number of carbon atoms, i.e. a $C_2$, $C_4$, $C_6$, $C_8$, $C_{10}$ or $C_{12}$ chain.

Such compounds are for example:

N,N,N',N'-tetraethyl-6,6"-(2,2':6',2"-terpyridine)diamide, which fits the general formula (I) wherein $R^1=R^2=C_2H_5$ while $R^3=R^4=H$;

N,N,N',N'-tetrabutyl-6,6"-(2,2':6',2"-terpyridine)diamide, which fits the general formula (I) wherein $R^1=R^2=C_4H_9$ while $R^3=R^4=H$; and N,N,N',N'-tetraoctyl-6,6"-(2,2':6',2"-terpyridine)diamide, which corresponds to the compound of general formula (I) wherein $R^1=R^2=C_8H_{17}$ while $R^3=R^4=H$.

However, compounds of general formula (I) in which $R^1$ and $R^2$ do not have the same meaning such as, for example, N,N'-diethyl-N,N'-diphenyl-6,6"-(2,2':6',2"-terpyridine)diamide, which fits the general formula (I) in which $R^1$ represents a phenyl group while $R^2$ represents an ethyl group, may also be very appropriate.

The object of the invention is also a method for synthesizing a compound as defined earlier, which comprises the reaction of a compound of general formula (II) hereafter:

(II)

wherein $R^3$ and $R^4$, either identical or different, have the same meaning as in the general formula (I), with an amine of formula of $HNR^1R^2$, wherein $R^1$ and $R^2$, either identical or different, have the same meaning as in the general formula (I), in the presence of a peptide coupling agent and a peptide coupling catalyst.

According to the invention, this reaction may be conducted by using any coupling agent and any coupling catalyst, the use of which has been proposed for peptide synthesis. Thus, it is notably possible to use 1-ethyl-3-[3-dimethylaminopropyl] carbodiimide hydrochloride as a coupling agent and N-hydroxy-benzotriazole as a coupling catalyst, in solution in a dipolar and aprotic organic solvent such as, for example, anhydrous dimethylformamide.

The compound of general formula (II) may be obtained by hydrolysis of the corresponding 2,2':6',2"-terpyridine-6,6"-dicarbonitrile in a hydro-alcoholic basic medium and by treating the product resulting from the hydrolysis to reflux of a sulfuric acid and acetic acid solution, as described by C. Galaup et al. in *Journal of Organic Chemistry* 2005, 70(6), 2274-2284 (reference [3]).

2,2':6',2"-terpyridine-6,6"-dicarbonitrile may be obtained by reaction of the corresponding 2,2':6',2"-terpyridine-1,1"-dioxide with cyanotrimethyl-silane in the presence of benzoyl chloride, as described by W. K. Fife in *Journal of Organic Chemistry* 1983, 48(8), 1375-1377 (reference [4]), while 2,2':6',2"-terpyridine-1,1"-dioxide may itself be obtained by oxidation of the nitrogen atom of each of the side pyridine rings of the corresponding 2,2':6',2"-terpyridine with meta-chloroperbenzoïc acid, as described by R. P. Thummel and Y. Jahng in *Journal of Organic Chemistry* 1985, 50(19), 3635-3636 (reference [5]).

If said 2,2':6',2"-terpyridine is substituted in the positions 4, 4' et 4", i.e. $R^3$ and $R^4$ are different from a hydrogen atom, and if $R^3$ is different from an alkoxy group, or if said 2,2':6', 2"-terpyridine is only substituted in the position 4', i.e. $R^3$ is different from a hydrogen atom but $R^4$ is a hydrogen atom, and if $R^3$ is different from an alkoxy group, then the latter may be obtained by the method described by F. H. Case and T. J. Kasper in *Journal of the American Chemical Society* 1956, 78, 5842-5844 (reference [6]), i.e. by reaction of a 2-acetylpyridine functionalized in the position 4 by the desired group $R^4$ with the aldehyde $R^3$CHO substituted with the desired group $R^3$, in the presence of ammonium acetate and ammonia in an aqueous solution, at a high temperature.

If said 2,2':6',2"-terpyridine is substituted in the positions 4' with an alkoxy group, i.e. $R^3$ is an alkoxy group, then the latter may be obtained by reaction of 4'-chloro-2,2':6',2"-terpyridine functionalized in the 4 and 4" positions by the desired group $R^4$ with an alcohol of formula R—OH, wherein R represents a $C_1$-$C_{12}$ alkyl chain, in dimethylsulfoxide and in the presence of potassium hydroxide, as described by G. R. Newkome et al. in *Journal of the Chemical Society, Chemical Communications* 1993, 925-927 (reference [7]).

The 4'-chloro-2,2':6',2"-terpyridine functionalized in the 4 and 4" positions by the desired group $R^4$ is itself prepared in three steps under the conditions described by E. C. Constable et al. in *Journal of the Chemical Society, Dalton Transactions* 1990, 1405-1409 (reference [8]). In this case, first of all, acetone is reacted with an excess of ethyl 2-pyridinyl-carboxylate functionalized in position 4 by the desired group $R^4$ in order to obtain the corresponding 1,3,5-trione intermediate which, by reaction with ammonium acetate allows then obtaining 4'-hydroxy-2,2':6',2"-terpyridine functionalized in positions 4 and 4" by the desired group $R^4$. The latter is then chlorinated with phosphorus pentachloride or phosphorus oxychloride.

The compounds according to the invention were found to have affinity for actinides and this, regardless of their degree of oxidation: III, IV, V or VI. Further, this affinity is greater than the one they have towards lanthanides.

Moreover, the compounds according to the invention were found to be capable of extracting the whole of the actinides of an acid aqueous phase and in particular, from a strongly acid aqueous phase such as a nitric acid solution with a molarity greater than or equal to 2.

Consequently, the object of the invention is further the use of a compound as defined earlier as a ligand of actinides and in particular for extracting actinide(s) of an acid aqueous solution by the liquid-liquid extraction technique.

Within the scope of this use, the compound may notably be used for separating the actinides present in an acid aqueous solution from the lanthanides which are also present in this solution.

According to the invention, the acid aqueous solution is preferably a solution of nitric acid with a molarity at least equal to 2.

Such an aqueous solution is, for example, a solution stemming from the dissolution of a used nuclear fuel in nitric acid.

However, this may also be an aqueous solution stemming from the dissolution of a used nuclear fuel in nitric acid but after having cleared it of the uranium which it contains.

In every case, the compound is advantageously used in solution, in an amount from 0.1 to 2 mol/L in an organic solvent, which is preferably selected from n-octanol, nitrobenzene, n-dodecane and hydrogenated tetrapropylene (or HTP).

Typically, the use of the compound for separating actinides from the lanthanides present in an acid aqueous solution comprises:
extraction of the actinides from the aqueous solution by putting it into contact with an organic phase comprising this compound in an organic diluent of the type of those mentioned earlier and then separating said aqueous solution and said organic phase; and stripping of the actinides present in the organic phase obtained at the end of the extraction by putting this phase into contact with an acid aqueous phase, preferably with a pH ranging from 2 to 3.

Other features and advantages of the invention will become better apparent upon reading the additional description which follows, which relates to examples of synthesis of compounds according to the invention and of demonstration of their capability of being used for extracting the actinides from a strongly acid solution and for separating them from the lanthanides which are also found in this solution.

Of course, these examples are only given as illustrations of the object of the invention and by no means are a limitation of this object.

DETAILED DESCRIPTION OF CERTAIN ILLUSTRATIVE EMBODIMENTS

Example 1

Synthesis of Compounds According to the Invention

The compounds according to the invention are synthesized from 2,2':6',2"-terpyridine-6,6"-dicarboxylic acid, noted hereafter as compound 4, which is obtained beforehand from 2,2':6',2"-terpyridine, noted hereafter as compound 1, according to the following reaction scheme:

Compound 1 is available commercially.

Compound 2 is first of all obtained by oxidation of the nitrogen atom of the two side pyridine rings of compound 1 with 4 equivalents of meta-chloroperbenzoïc acid (or m-CPBA) under the conditions described in the aforementioned reference [5] (yield: 73%).

Next compound 3 is obtained by reacting the compound 2 with 10 equivalents of cyanotri-methylsilane (or Me$_3$SiCN) in the presence of 4 equivalents of benzoyl chloride (or PhCOCl) under the conditions described in the aforementioned reference [4] (yield: 88%).

Compound 3 is then hydrolyzed in a hydro-alcoholic basic medium (KOH/ethanol/H$_2$O) before being subject to treatment with reflux of a sulfuric acid and acetic acid solution as described in the aforementioned reference [3] (yield: 96%).

1.1. Synthesis of N,N,N',N'-tetraethyl-6,6"-(2,2':6', 2"-terpyridine)diamide The title compound, noted hereafter as TETPYDA, is obtained by reacting compound 4 with N,N-diethylamine.

To do this, 350 mg (1.1 mmol) of the compound 4 and 100 mg of N-hydroxybenzotriazole (or HOBt—0.7 mmol) are dissolved in 3 mL of anhydrous DMF. Next, 440 mg of 1-ethyl-3-[3-dimethylamino-propyl]carbodiimide hydrochloride (or EDC—2.3 mmol) and 237 µL of N,N-diethylamine (2.3 mmol) are added to this solution and the resulting mixture is stirred for 18 hours, at room temperature and under an argon atmosphere. After evaporation of the solvent, the crude product is taken up in CH$_2$Cl$_2$ and washed three times with distilled water. The organic phase is then dried on MgSO$_4$ and the solvent is evaporated. The obtained residue is purified by chromatography on silica gel (elution with a CH$_2$Cl$_2$/MeOH 95:5 mixture in isocratic mode).

After evaporation of the solvents, 300 mg of TETPYDA are obtained (yield: 64%) in the form of a white powder which consists of a mixture of two rotamers each representing 50% by mass of this mixture.

Empirical formula: C$_{25}$H$_{29}$N$_5$O$_2$
Molar mass: 431 g/mol
Melting point: 132° C.
$^1$H MNR (300 MHz, CDCl$_3$):
rotamer 1: δ ppm: 8.66 (dd, $^3$J=7.8, $^4$J=0.9, 2H, H$_{pyridine}$), 8.46 (d, $^3$J=7.8, 2H, H$_{pyridine}$), 7.97 (t, $^3$J=7.8, 2H, H$_{pyridine}$), 7.94 (t, $^3$J=7.8, 1H, H$_{pyridine}$), 7.66 (dd, $^3$J=7.8, $^4$J=0.9, 2H, H$_{pyridine}$), 3.63 (q, $^3$J=7.0, 8H, CH$_2$), 1.32 (t, $^3$J=7.0, 12H, CH$_3$)

rotamer 2: all the signals coincide with the rotamer 1 except those at 3.47 (q, $^3$J=7.0, 8H, CH$_2$), 1.27 (t, $^3$J=7.0, 12H, CH$_3$)

$^{13}$C NMR (75 MHz, CDCl$_3$):
rotamer 1: δ ppm: 168.5 (2C=O), 154.9 (2Cq), 154.5 (4Cq), 137.9 (2CH$_{pyridine}$), 137.7 (CH$_{pyridine}$), 123.4 (2CH$_{pyridine}$), 121.4 (2CH$_{pyridine}$), 121.3 (2CH$_{pyridine}$), 40.3 (4CH$_2$), 12.9 (4CH$_3$)

rotamer 2: all the signals coincide with those of rotamer 1 except for the signals at 43.3 (4CH$_2$), 14.5 (4CH$_3$)

Mass spectrometry (EI), m/z (n): 431 (M$^+$, 30%), 232 (M$^+$-2CONEt$_2$, 82%), 72 ($^+$NEt$_2$, 100%)

HPLC purity at 210 nm: 99.6%

The crystallographic structure of TETPYDA as well as that of the complex formed by this compound after reaction with one equivalent of neodymium(III) nitrate were resolved by X-ray diffraction. Their ORTEP representation is illustrated in FIGS. 1 and 2.

The crystals of TETPYDA and of its complex with neodymium(III) were obtained in methanol by slow evaporation.

Figure 1:
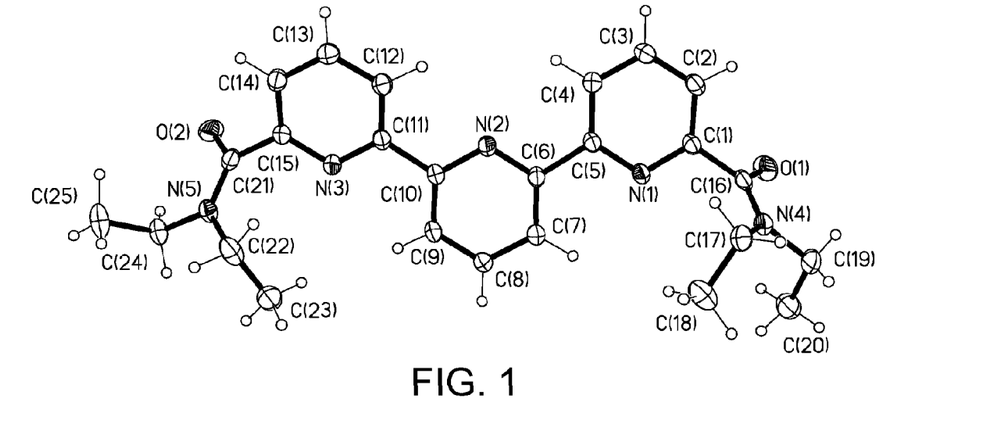
FIG. 1 corresponds to the ORTEP representation of the crystallographic structure of a first compound according to the invention, as resolved by X-ray diffraction.
Figure 2:
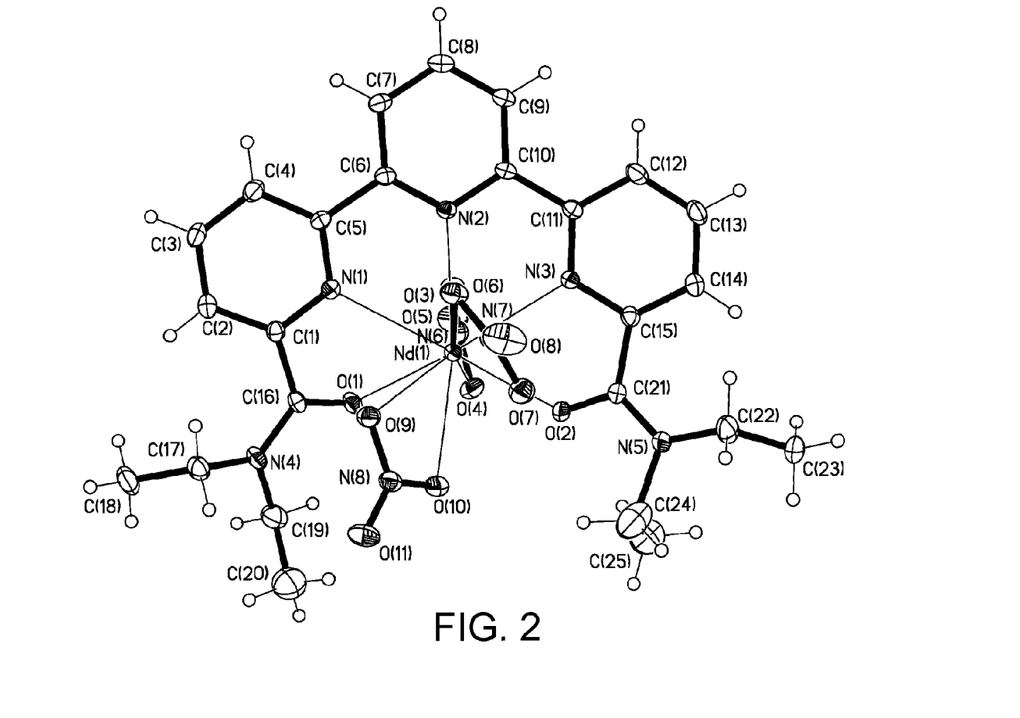
FIG. 2 corresponds to the ORTEP representation of the crystallographic structure of the complex formed by the compound of FIG. 1 and neodymium(III), as resolved by X-ray diffraction.

FIG. 1 shows that in the crystalline state, TETPYDA in the s-trans conformation is not pre-arranged with view to complexation since the nitrogen atoms of the pyridine rings are in positions opposite to each other and the carbonyl functions are oriented practically perpendicularly to the plane of these rings, while FIG. 2 shows that after complexation, TETPYDA is pentadented and forms a 1:1 stoichiometric complex with neodymium(III). The latter is complexed as an internal sphere both by the (hard) oxygen atoms of the amide groups and by the nitrogen atoms of the pyridine rings (softer according to Pearson's theory).

1.2. Synthesis of N,N,N',N'-tetrabutyl-6,6"-(2,2':6', 2"-terpyridine)diamide The title compound, noted hereafter as TBTPYDA, is obtained by reaction of compound 4 with N,N-dibutylamine.

To do this, 1.4 g (4.3 mmol) of the compound 4 and 383 mg of HOBT (2.5 mmol) are dissolved in 13 mL of anhydrous DMF. Next 1.7 g of EDC (9.0 mmol) and 1.5 mL of N,N-dibutylamine (9.0 mmol) are added to the solution and the resulting mixture is stirred for 18 hours at room temperature and under an argon atmosphere. After evaporation of the solvent, the crude product is taken up in $CH_2Cl_2$ and washed with a 1N HCl aqueous solution and then with a 5% sodium bicarbonate aqueous solution. The organic phase is then dried on $MgSO_4$ and the solvent is evaporated. The obtained residue is purified by chromatography on silica gel (elution with a $CH_2Cl_2$/ethyl acetate mixture in an elution gradient mode) and recrystallized from petroleum ether.

970 mg of TBTPYDA are thereby obtained (yield: 42%) in the form of a white powder which consists of a mixture of two rotamers each representing 50% by mass of this mixture.

Empirical formula: $C_{33}H_{45}N_5O_2$
Molar mass: 543 g/mol
Melting point: 105° C.
$^1H$ MNR (400 MHz, $CDCl_3$):
rotamer 1: δ ppm: 8.67 (d, $^3J=8.1$, 2H, $H_{pyridine}$), 8.45 (d, $^3J=8.1$, 2H, $H_{pyridine}$), 8.02-7.85 (m, 3H, $H_{pyridine}$) 7.64 (d, $^3J=7.5$, 2H, $H_{pyridine}$), 3.56 (t, $^3J=7.5$, 8H, $CH_2$), 1.81-1.59 (m, 8H, $CH_2$), 1.54-1.36 (m, 8H, $CH_2$), 1.01 (t, $^3J=7.2$, 12H, $CH_3$)
rotamer 2: All the signals coincide with those of the rotamer 1 except the signals at 3.40 (t, $^3J=7.5$, 8H, $CH_2$), 1.81-1.59 (m, 8H, $CH_2$), 1.21-1.06 (m, 8H, $CH_2$) et 0.77 (t, $^3J=7.2$, 12H, $CH_3$)
Mass spectrometry (ESI), m/z (1%): 544 ($MH^+$, 52%), 566 ($MNa^+$, 36%)
HPLC purity at 210 nm: 99.9%

1.3. Synthesis of N,N,N',N'-tetraoctyl-6,6"-(2,2':6',2"-terpyridine)diamide

The title compound, noted hereafter as TOTPYDA, is obtained by reaction of compound 4 with N,N-dioctylamine.

To do this, 320 mg (1.0 mmol) of the compound 4 and 92 mg of HOBT (0.6 mmol) are dissolved in 3 mL of anhydrous DMF. Next, 400 ml of EDC (2.1 mmol) in 642 μL of N,N-dioctylamine (2.1 mmol) are added to the solution and the resulting mixture is stirred for 18 hours, at room temperature and under an argon atmosphere. After evaporation of the solvent, the crude product is taken up in $CH_2Cl_2$ and washed three times with distilled water. The organic phase is then dried on $MgSO_4$ and the solvent is evaporated. The obtained residue is purified by chromatography on silica gel (elution with petroleum ether, and then with a petroleum ether/ethyl acetate 80:20 mixture in an isocratic mode).

After evaporation of the solvents, 565 mg of TOTPYDA are obtained (yield: 74%) in the form of a yellow oil which consists of a mixture of two rotamers each representing 50% by mass of this mixture.

Empirical formula: $C_{49}H_{77}N_5O_2$
Molar mass: 768 g/mol
$^1H$ NMR (300 MHz, $CDCl_3$):
rotamer 1: δ ppm: 8.66 (dd, $^3J=7.8$, $^4J=0.9$, 2H, $H_{pyridine}$), 8.44 (d, $^3J=7.8$, 2H, $H_{pyridine}$), 7.94 (t, $^3J=7.8$, 2H, $H_{pyridine}$), 7.91 (t, $^3J=7.8$, 1H, $H_{pyridine}$) 7.62 (dd, $^3J=7.8$, $^4J=0.9$, 2H, $H_{pyridine}$), 3.54 (t, $^3J=7.8$, 8H, $CH_2$), 1.73-1.68 (m, 8H, $CH_2$), 1.38-1.12 (m, 40H, $CH_2$), 0.90 (t, $^3J=6.6$, 12H, $CH_3$)
rotamer 2: All the signals coincide with those of rotamer 1 except for the signals at 3.39 (t, $^3J=7.8$, 8H, $CH_2$), 1.12 (m, 40H, $CH_2$) and 0.79 (t, $^3J=6.6$, 12H, $CH_3$)
$^{13}C$ NMR (75 MHz, $CDCl_3$):
rotamer 1: δ ppm: 168.7 (2C=O), 154.8 (2Cq), 154.7 (2Cq), 154.4 (2Cq), 137.7 ($3CH_{pyridine}$), 123.4 ($2CH_{pyridine}$), 121.3 ($2CH_{pyridine}$), 121.2 ($2CH_{pyridine}$), 46.0 ($4CH_2$), 31.8-22.5 ($20CH_2$), 27.6 ($4CH_2$), 14.0 ($4CH_3$)
rotamer 2: All the signals coincide with those of rotamer 1 except the signals at 49.0 ($4CH_2$) and 14.1 ($4CH_3$)

Mass spectrometry (CI), m/z (1%): 769 ($MH^+$, 85%)
HPLC purity at 210 nm: 99.0%

1.4. Synthesis of N,N'-diethyl-N,N'-diphenyl-6,6"-(2,2':6',2"-terpyridine)diamide The title compound, noted hereafter as DEDPTPYDA is obtained by reaction of compound 4 with N-ethyl-N-phenylamine.

To do this, 1.2 g (3.8 mmol) of the compound 5 and 355 mg of HOBt (2.2 mmol) are dissolved in 11 mL of anhydrous DMF. Next 1.5 g of EDC (7.9 mmol) and 994 μL of N-ethyl-N-phenylamine (7.9 mmol) are added to this solution and the resulting mixture is stirred for 18 hours at room temperature and under an argon atmosphere. After evaporation of the solvent, the crude product is taken up in $CH_2Cl_2$ and washed with a 1N hydrochloric acid aqueous solution and then with a 5% sodium bicarbonate aqueous solution. The organic phase is then dried on $MgSO_4$ and the solvent is evaporated. The obtained residue is then purified by chromatography on silica gel (elution with a $CH_2Cl_2$/ethyl acetate mixture in an elution gradient mode) and recrystallized from petroleum ether.

890 mg of DEDPTPYDA are thereby obtained (yield: 44%) in the form of a white powder which consists of a mixture of 2 rotamers each representing 50% by mass of this mixture.

Empirical formula: $C_{33}H_{29}N_5O_2$
Molar mass: 527 g/mol
Melting point: 168° C.
$^1H$ NMR (400 MHz, $CDCl_3$):
δ ppm: 8.36 (d, $^3J=4.6$, 2H, $H_{pyridine}$), 7.70 (m, 7H, $H_{pyridine}$) 7.17 (m, 10H, $H_{phenyl}$), 4.06 (q, $^3J=7.2$, 4H, $CH_2$), 1.28 (d, $^3J=7.2$, 6H, $CH_3$)
Mass spectrometry (ESI), m/z (1%): 528 ($MH^+$, 28%), 550 ($MNa^+$, 61%)
HPLC purity at 210 nm: 99.4%

Example 2

Extractant Properties of the Compounds According to the Invention

2.1. Demonstration of the Extractant Properties of the Compounds According to the Invention Extractions were carried out by using:
as organic phases: solutions either comprising TOTPYDA or TETPYDA at 0.10 mol/L in n-octanol; and
as aqueous phases: four aqueous solutions designated hereafter as S1, S2, S3 and S4 and respectively comprising:
S1: a mixture of $^{239-240}$Pu(IV), $^{244}$Cm(III), $^{241}$Am(III), $^{152}$Eu(III) and $^{139}$Ce(III), all in trace amounts ($10^{-5}$-$10^{-6}$ mol/L), and nitric acid at 2.8 or 2.9 mol/L;
S2: $^{238}$U(VI) at 0.01 mol/L and nitric acid at 2.6 mol/L;
S3: $^{237}$Np (V) at 0.01 mol/L, 6% of $^{237}$Np(VI) based on the total mass of $^{237}$Np, and nitric acid at 3.0 mol/L;
S4: $^{237}$Np(VI) at 0.01 mol/L and nitric acid at 3.0 mol/L of nitric acid.

Each of the aqueous phases S1-S4 is put into contact in a tube with one of the organic phases, in an amount of 1 volume of aqueous phase for 1 volume of organic phase, and the thereby contacted phases are left with mechanical stirring for one hour at a constant temperature of 25° C.

After this, the aqueous and organic phases are separated from each other and the activities or concentrations of the different metal elements in these phases are determined by α spectrometry, γ spectrometry or X fluorescence depending on the case.

Figure 3:
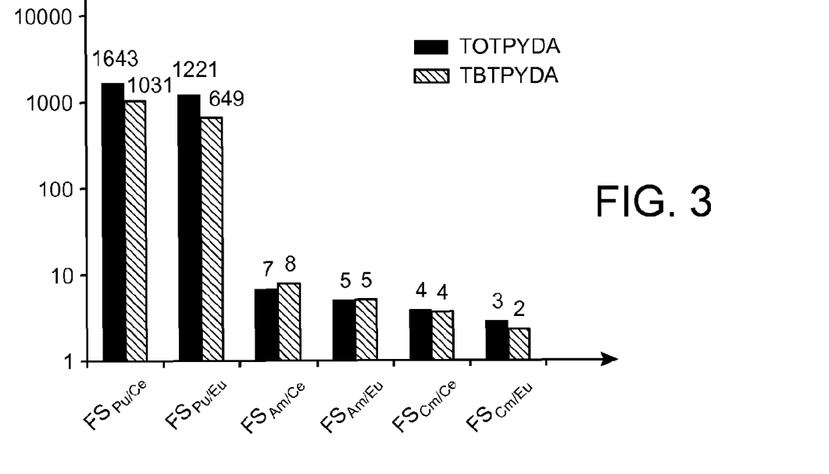
FIG. 3 represents in the form of a bar diagram, the separation factors $FS_{Pu/Ce}$, $FS_{Pu/Eu}$, $FS_{Am/Ce}$, $FS_{Am/Eu}$, $FS_{Cm/Ce}$ and $FS_{Cm/Eu}$ as obtained during extractions carried out on a nitric aqueous phase containing plutonium, americium, curium, europium and cerium, by means of two organic phases containing for the first, a second compound according to the invention (solid bars) and for the second, a third compound according to the invention (hatched bars) in n-octanol.

Table 1 hereafter shows for each extraction, the distribution coefficients obtained from the thereby determined activities or concentrations, while FIG. 3 shows for the extractions carried out on the aqueous phase S1, the separation factors $FS_{Pu/Ce}$, $FS_{Pu/Eu}$, $FS_{Am/Ce}$, $FS_{Am/Eu}$, $FS_{Cm/Ce}$ and $FS_{Cm/Eu}$ calculated from the distribution coefficients. In this figure, the solid bars correspond to the separation factors obtained for the extraction carried out with the organic phase containing TOTPYDA while the hatched bars correspond to the separation factors obtained for the extraction carried out with the organic phase containing TBTPYDA.

It is recalled that, in the field of liquid-liquid extractions, the distribution coefficient, noted as $D_M$, of an element M corresponds to the ratio at equilibrium, of the concentrations (or activities) of this element in the organic and aqueous phases having been put into contact, and that the separation factor between two metal elements M1 and M2, noted as $FS_{M1/M2}$, corresponds to $D_{M1}/D_{M2}$, i.e. to the ratio of the distribution coefficients of the metal elements M1 and M2 obtained during a same extraction.

TABLE I

| Aqueous phase | Element | $D_M$ TOTPYDA | $D_M$ TBTPYDA |
|---|---|---|---|
| S1 [HNO$_3$] 2.9M | $^{239\text{-}240}$Pu(IV) | 3.8 | — |
| | $^{241}$Am(III) | $1.5 \cdot 10^{-2}$ | — |
| | $^{244}$Cm(III) | $8.7 \cdot 10^{-3}$ | — |
| | $^{152}$Eu(III) | $3.1 \cdot 10^{-3}$ | — |
| | $^{139}$Ce(III) | $2.3 \cdot 10^{-3}$ | — |
| [HNO$_3$] 2.8M | $^{239\text{-}240}$Pu(IV) | — | 2.4 |
| | $^{241}$Am(III) | — | $1.8 \cdot 10^{-2}$ |
| | $^{244}$Cm(III) | — | $8.5 \cdot 10^{-3}$ |
| | $^{152}$Eu(III) | — | $3.7 \cdot 10^{-3}$ |
| | $^{139}$Ce(III) | — | $2.3 \cdot 10^{-3}$ |
| S2 | $^{238}$U(VI) | 0.31 | 0.46 |
| S3 | $^{237}$Np(V) | 0.78 | 1.04 |
| S4 | $^{237}$Np(VI) | 0.68 | 0.96 |

Table 1 and FIG. 3 show that plutonium is particularly well extracted from an acid aqueous phase with TOTPYDA and TBTPYDA since the distribution coefficients $D_{Pu}$, are greater than 2 and that the separation factors $FS_{Pu/Ce}$ and $FS_{Pu/Eu}$ are greater than 500.

The elements with a degree of oxidation of VI (uranium and neptunium) are also efficiently extracted since they have distribution coefficients comprised between 0.3 and 1.0.

As regards Np(V), as the phase S3 used contains 6% of Np(VI), the obtained distribution coefficients are not exactly representative of Np(V) alone. They show that TOTPYDA and TBTPYDA are capable of extracting from a strongly acid aqueous solution a mixture of Np(V) and Np(VI), which is of great interest since neptunium is present in the dissolution solutions of used nuclear fuels with degrees of oxidation of V and VI. Therefore it will not be necessary to reduce Np(VI) into Np(IV), a form which is often better extracted with the extractants of the state of the art.

Moreover, as shown in FIG. 3, TOTPYDA and TBTPYDA have greater affinity for actinides(III) than for lanthanides since the separation factors $FS_{Am/Ce}$, $FS_{Am/Eu}$, $FS_{Cm/Ce}$ and $FS_{Cm/Eu}$ are all greater than or equal to 2.

With an organic phase containing TOTPYDA or TBT-PYDA at 0.10 mol/L in n-octanol, it is therefore possible to separate all the actinides present in a strongly acid aqueous solution from the lanthanides also present in this solution. If it is true that elements with a degree of oxidation IV, V or VI are particularly well extracted, separation of the actinides(III) from the lanthanides is also ensured.

2.2. Influence of the Concentration of the Compound According to the Invention in the Organic Phase Extractions are carried out by using:
as organic phases: solutions comprising TOTPYDA at 0.05, 0.10, 0.25, 0.50 and 1 mol/L in n-octanol; and
as aqueous phases: aqueous solutions comprising a mixture of $^{29\text{-}240}$Pu(IV), $^{244}$Cm(III), $^{241}$Am(III), $^{152}$Eu(III) and $^{139}$Ce(III), all in trace amounts ($10^{-5}$-$10^{-6}$ mol/L), and nitric acid at 2.9 mol/L.

As earlier, each organic phase is put into contact with one of the aqueous phases in a tube, in an amount of 1 volume of organic phase for 1 volume of aqueous phase and the thereby contacted phases are left with mechanical stirring for one hour at a constant temperature of 25° C.

After this, the aqueous and organic phases are separated from each other and the activities or concentrations of the different metal elements in these phases are determined by α spectrometry or by γ spectrometry depending on the case.

Figure 4:
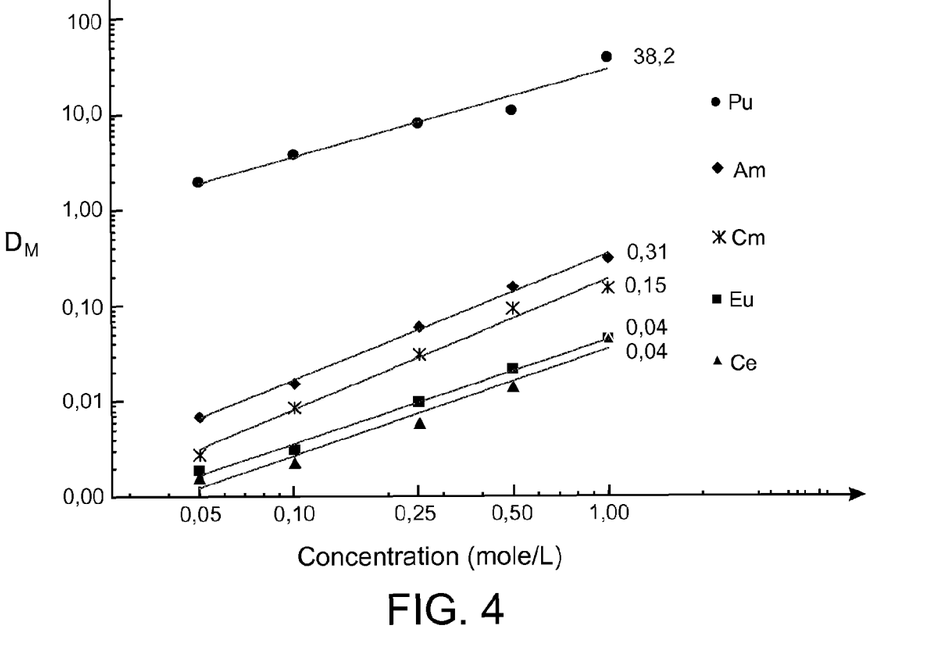
FIG. 4 illustrates the variation of the distribution coefficients ($D_M$) of plutonium, americium, curium, europium and cerium as obtained during extractions carried out on nitric aqueous phases containing plutonium, americium, curium, europium and cerium, by means of organic phases containing the second compound according to the invention in n-octanol, versus the concentration of this compound in said organic phases.

FIG. 4 illustrates the change in the distribution coefficients obtained from the thereby determined activities or concentrations, depending on the concentration of TOTPYDA in the organic phase.

The increase in the TOTPYDA concentration of the organic phase therefore gives the possibility of significantly improving the extraction of actinides(III) while retaining better affinity for actinides(III) as compared with lanthanides (III).

Further, the slopes of the extrapolation lines $\log(D_M)=f(\log [\text{extractant}])$ are approximately equal to 1, which confirms that the complexes formed during the extraction set into play a ligand molecule for an actinide or lanthanide cation (1:1 stoichiometry) as this is observed in the crystalline state by X-ray diffraction.

2.3. Influence of the Polarity of the Diluent of the Organic Phase

An extraction is carried out while proceeding in the same way as in 2.1 and 2.2 hereinbefore but by using:
as an organic phase: a solution comprising 1 mol/L of TBTPYDA in nitrobenzene which is a more polar solvent than n-octanol; and
as an aqueous phase: an aqueous solution comprising a mixture of $^{239\text{-}240}$Pu(IV), $^{244}$Cm(III), $^{241}$Am(III), $^{152}$Eu (III) and $^{139}$Ce(III), all in trace amounts ($10^{-5}$-$10^{-6}$ mol/L), and nitric acid at 3.1 mol/L.

Under these conditions, the obtained distribution coefficients are clearly greater than those obtained by using 0.1 mol/L of TBTPYDA in solution in n-octanol and than those obtained with 1 mol/L of TOTPYDA in solution in n-octanol since these coefficients are 121 for plutonium, 3 for americium, 1.3 for curium, 0.25 for europium and 0.36 for cerium, respectively.

Figure 5:
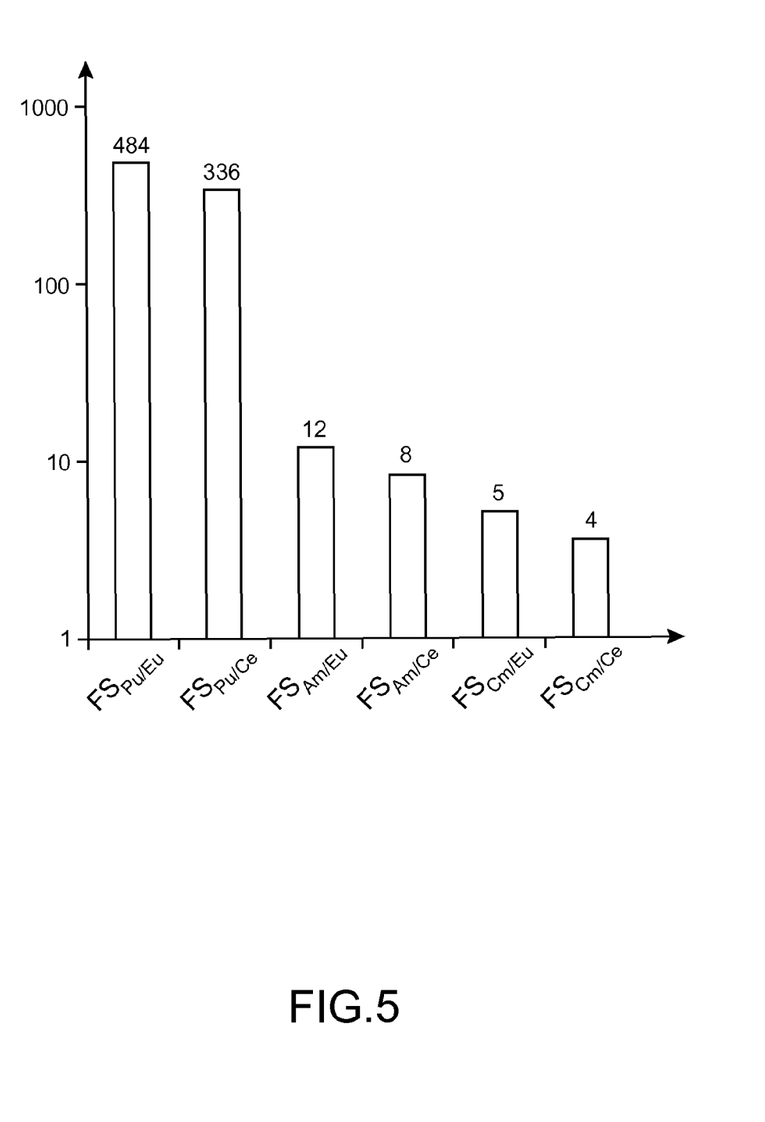
FIG. 5 illustrates in the form of a bar diagram, the separation factors $FS_{Pu/Ce}$, $FS_{Pu/Eu}$, $FS_{Am/Ce}$, $FS_{Am/Eu}$, $FS_{Cm/Ce}$ and $FS_{Cm/Eu}$ as obtained during extractions carried out on a nitric aqueous phase containing plutonium, americium, curium, europium and cerium, by means of an organic phase containing the third compound according to the invention in nitrobenzene.

Moreover, as shown in FIG. 5, which illustrates the separation factors $FS_{Pu/Ce}$, $FS_{Pu/Eu}$, $FS_{Am/Ce}$, $FS_{Am/Eu}$, $FS_{Cm/Ce}$ and $FS_{Cm/Eu}$ calculated from these distribution coefficients, the separation factors $FS_{Am/Ce}$, $FS_{Am/Eu}$, $FS_{Cm/Ce}$ and $FS_{Cm/Eu}$ are also clearly greater.

By increasing the polarity of the diluent of the organic phase, it is therefore possible to significantly improve extraction of actinides(III) and their separation from lanthanides.

CITED REFERENCES

[1] PCT International Application WO 2007/118904
[2] PCT International Application WO 2008/049807
[3] C. Galaup et al., *Journal of Organic Chemistry* 2005, 70(6), 2274-2284
[4] W. K. Fife, *Journal of Organic Chemistry* 1983, 48(8), 1375-1377
[5] R. P. Thummel and Y. Jahng, *Journal of Organic Chemistry* 1985, 50(19), 3635-3636
[6] F. H. Case and T. J. Kasper, *Journal of the American Chemical Society* 1956, 78, 5842-5844
[7] G. R. Newkome et al., *Journal of the Chemical Society, Chemical Communications* 1993, 925-927
[8] E. C. Constable et al., *Journal of the Chemical Society, Dalton Transactions* 1990, 1405-1409

What is claimed is:

1. A compound which fits the general formula (I) hereafter:

(I)

wherein:
  $R^1$ and $R^2$, either identical or different, represent (a) a hydrogen atom, (b) a linear or branched non-cyclic saturated or unsaturated $C_1$-$C_{12}$ hydrocarbon group, (c) a phenyl group, a benzyl group, a biphenyl group or a tolyl group;
  $R^3$ represents (a) a hydrogen atom, (b) a linear or branched non-cyclic saturated or unsaturated $C_1$-$C_{12}$ hydrocarbon group, (c) a phenyl group, a tolyl group or a linear or branched $C_1$-$C_{12}$ alkoxy group; and
  $R^4$ represents (a) a hydrogen atom, (b) a linear or branched non-cyclic saturated or unsaturated $C_1$-$C_{12}$ hydrocarbon group, (c) a phenyl group or a tolyl group.

2. The compound of claim 1, which fits the general formula (I) wherein:
  $R^1$ and R2, either identical or different, represent a hydrogen atom, a linear or branched C1-C12 alkyl chain or a phenyl group;
  R3 represents a hydrogen atom or a linear or branched $C_1$-$C_{12}$ alkyl or alkoxy group; and
  R4 represents a hydrogen atom or a linear or branched $C_1$-$C_{12}$ alkyl group.

3. The compound of claim 1, which fits general formula (I) wherein $R^3$ and $R^4$ represent a hydrogen atom.

4. The compound of claim 1, which fits general formula (I) wherein $R^1$ and $R^2$ are identical with each other.

5. The compound of claim 4, which fits general formula (I) wherein $R^1$ and $R^2$ represent a linear or branched $C_1$-$C_{12}$ alkyl chain.

6. The compound of claim 1, which is selected from:
  N,N,N',N'-tetraethyl-6,6"-(2,2':6',2"-terpyridine)diamide;
  N,N,N',N'-tetrabutyl-6,6"-(2,2':6',2"-terpyridine)diamide; and
  N,N,N',N'-tetraoctyl-6,6"-(2,2':6',2"-terpyridine)diamide.

* * * * *